United States Patent
Ding et al.

(10) Patent No.: US 10,586,609 B2
(45) Date of Patent: Mar. 10, 2020

(54) MANAGING GENE SEQUENCES

(71) Applicant: INTERNATIONAL BUSINESS MACHINES CORPORATION, Armonk, NY (US)

(72) Inventors: Jian Dong Ding, Shanghai (CN); Sheng Huang, Shanghai (CN); Junchi Yan, Shanghai (CN); Ya Nan Zhang, Shanghai (CN); Jun Zhu, Shanghai (CN)

(73) Assignee: International Business Machines Corporation, Armonk, NY (US)

( * ) Notice: Subject to any disclaimer, the term of this patent is extended or adjusted under 35 U.S.C. 154(b) by 711 days.

(21) Appl. No.: 14/926,051

(22) Filed: Oct. 29, 2015

(65) Prior Publication Data

US 2016/0132636 A1  May 12, 2016

(30) Foreign Application Priority Data

Oct. 30, 2014 (CN) .......................... 2014 1 0599394

(51) Int. Cl.
  *G16B 30/00*  (2019.01)
(52) U.S. Cl.
  CPC .................................. *G16B 30/00* (2019.02)
(58) Field of Classification Search
  CPC ........................................................ G06F 19/22
  See application file for complete search history.

(56) References Cited

U.S. PATENT DOCUMENTS 6,401,043 B1 * 6/2002 Stanton, Jr. ............ G16B 30/00
                                                    702/20
8,032,310 B2 * 10/2011 Stenger ................ C12Q 1/6888
                                                    702/20

(Continued)

FOREIGN PATENT DOCUMENTS

CN      1530668 A    9/2004
CN    103093121 A    5/2013

(Continued)

OTHER PUBLICATIONS

Jones, Daniel et. al., Compression of next-generation sequencing reads aided by highly efficient de novo assembly, Nucleic Acids Research, Aug. 16, 2012, 9 pgs., vol. 40-No. 22, Oxford University Press, published online <http://www.ncbi.nlm.nih.gov/pmc/articles/PMC3526293/pdf/gks754.pdf/>.

Liu, Yongchao et. al., Parallelized short read assembly of large genomes using de Bruijn graphs, BMC Bioinformatics, Aug. 25, 2011,10 pgs., vol. 12:354, BioMed Central Ltd., published online <http://www.biomedcentral.com/content/pdf/1471-2105-12-354.pdf/>.

(Continued)

*Primary Examiner* — Aaron A Priest
(74) *Attorney, Agent, or Firm* — Joseph Petrokaitis

(57) ABSTRACT

A method and apparatus for determining similarity among gene sequences, for compressing a gene sequence, and for decompressing a gene sequence. The method for determining similarity between a first gene sequence and a second gene sequence includes: moving a sliding window of a predefined length on the first gene sequence and the second gene sequence respectively; extracting a first part $String1_i$ of the first gene sequence within the sliding window, and a second part $String2_i$ of the second gene sequence within the sliding window during the $i^{th}$ movement of the sliding window; and determining similarity between the first gene sequence and the second gene sequence based on the first part $String1_i$ and the second part $String2_i$. Also provided is an apparatus for the above method.

13 Claims, 9 Drawing Sheets

(56) References Cited

U.S. PATENT DOCUMENTS

| | | | |
|---|---|---|---|
| 8,594,951 B2 | 11/2013 | Homer | |
| 2008/0215251 A1* | 9/2008 | Selinger | G06F 19/22 702/20 |
| 2013/0031092 A1 | 1/2013 | Bhola et al. | |
| 2013/0166518 A1 | 6/2013 | Mande et al. | |
| 2013/0204851 A1 | 8/2013 | Bhola et al. | |
| 2013/0311435 A1 | 11/2013 | Freidlander et al. | |
| 2014/0108323 A1 | 4/2014 | Leighton et al. | |
| 2014/0244644 A1* | 8/2014 | Mashinchi | G06F 17/30595 707/737 |

FOREIGN PATENT DOCUMENTS

| | | |
|---|---|---|
| JP | 200400018 A | 1/2004 |
| WO | 2013006776 A2 | 1/2013 |

OTHER PUBLICATIONS

Zhao, Kun et. al., A dynamic hashing approach to build the de bruijn graph for genome assembly, TENCON 2013—2013 IEEE Region 10 Conference, Oct. 22, 2013, pp. 1-4, IEEE, Xi'An, China <http://ieeexplore.ieee.org/xpl/articleDetails.jsp?arnumber=6719008/>.

Zhao, Kun et. al, Accelerating De Bruijn Graph-Based Genome Assembly for High-Throughput Short Read Data, 2013 International Conference on Parallel and Distributed Systems (ICPADS), Dec. 15, 2013, pp. 426-427, IEEE, Seoul, South Korea <http://ieeexplore.ieee.org/xpl/articleDetails.jsp?arnumber=6808205/>.

Somboonsak, P. et al., "A New Edit Distance Method for Finding Similarity in Dna Sequence", World Academy of Science, Engineering an Technology, International Journal of Biological, Biomolecular, Agricultural, food and Biotechnological Engineering, vol. 5, No. 10, 2011, 5 pages.

* cited by examiner

MANAGING GENE SEQUENCES

CROSS REFERENCE TO RELATED APPLICATION

This application claims priority under 35 U.S.C. § 119 from Chinese Patent Application No. 201410599394.7 filed Oct. 30, 2014, the entire contents of which are incorporated herein by reference.

TECHNICAL FIELD OF THE INVENTION

Various embodiments of the present invention relate to data management, and more specifically, to a method and apparatus for managing gene sequences.

BACKGROUND OF THE INVENTION

As the field of biology has developed, research on biological genes has gone deeper and deeper into various aspects such as human health, medicine research & development, new plant and animal species and microorganisms.

By sequencing a gene of an organism, it is possible to obtain a sequence of base pairs composing the chromosome of the organism. Usually the process of measuring a gene sequence of the first sample of a species is referred to as sequencing, while the process of measuring a gene sequence of other sample of the species is referred to as re-sequencing. A breakthrough has been achieved in sequencing and re-sequencing technologies. With various involved costs going increasingly lower, more and more individuals or organizations come to realize the significance of gene sequence, and so far gene sequence data of a large amount of species have been obtained through a sequencing/re-sequencing process.

Gene sequences include a large amount of data. As an example, human genes include about 3 billion base pairs or 6 billion individual characters (i.e. A, G, T, and C) according to existing representation modes. Therefore, each gene sequence stored in the gene database will take up a large amount of storage space. When there is a need to store a large amount of gene sequences or to copy and transmit the gene sequences, challenges arise regarding the data storage/data transmission efficiency.

Biologists have found similarities between gene sequences of various samples of the same species. For example, the similarity between human gene sequences is much higher than the similarity between gene sequences of humans and other species. Similarly, the similarity between gene sequences within one race is usually higher than the similarity between gene sequences of different races. Based on the similarity, there has been proposed a concept of reference gene sequence, which can be a representative typical gene sequence that has been obtained during past data processing.

For example, in human beings, gene sequences of males of a particular race might have some common parts controlling skin color, hair color and gender, which might be identical or only contain slight differences. Therefore, the gene sequence of a given male of a particular race can be used as the reference gene sequence. When the gene sequence of another male of the same race needs to be stored, it can be compared with the reference gene sequence, and only difference data among these two gene sequences and an identifier of the reference gene sequence have to be stored. Thereby, the data amount to be stored can be reduced greatly, and the objective of data compression can be achieved.

Note that since many parts in gene sequences of males of the same race are identical and the proportion of difference data is not very high, the above method can significantly reduce the data space for storing gene sequences. Therefore, a large quantity of reference gene sequences can be stored in the reference data repository, and a reference gene sequence that best matches a to-be-stored gene sequence can be selected from the reference data repository based on similarity search. However, due to characteristics of each gene sequence such as large data amounts and various combinations of individual base characters, the existing similarity search algorithm is not well suited for gene sequences.

How to determine similarity between two gene sequences is a basis for selecting a reference gene sequence and other subsequent treatment in the technical field of gene sequence treatment. Therefore, it now becomes a research focus in the gene sequence treatment field regarding how to provide a more effective method for determining similarity on the basis of features of gene sequences.

SUMMARY OF THE INVENTION

A more effective technical solution is desired for determining similarity between a first gene sequence and a second gene sequence by taking into full consideration inherent characteristics of gene sequences. Further, it is desired to find a reference gene sequence more matched to a to-be-stored gene sequence based on the method for determining similarity, so as to reduce the amount of difference data between the to-be-stored gene sequence and the reference gene sequence to achieve a better effect of data compression.

In one embodiment of the present invention, there is provided a computer-implemented method for determining similarity between a first gene sequence and a second gene sequence. The method includes: moving a sliding window having a predefined length on the first gene sequence and the second gene sequence respectively; extracting a first part $String1_i$ of the first gene sequence within the sliding window, and a second part $String2_i$ of the second gene sequence within the sliding window during the $i^{th}$ movement of the sliding window; and determining the similarity between the first gene sequence and the second gene sequence based on the first part $String1_i$ and the second part $String2_i$, thereby identifying the similarity of the first gene sequence and second gene sequence.

In another embodiment of the present invention, there is provided a computer-implemented method for compressing a gene sequence. The method includes: obtaining a gene sequence and at least one reference gene sequence; determining at least one similarity between the gene sequence and each of the at least one reference gene sequence; selecting the at least one reference gene sequence as a current reference gene sequence where the at least one similarity has a minimum value being less than or equal to a predefined threshold; and generating a compressed gene sequence, which includes an identifier of the current reference gene sequence and difference data between the gene sequence and the current reference gene sequence, thereby generating a compressed gene sequence.

In one embodiment of the present invention, there is provided a computer-implemented method for decompressing a compressed gene sequence. The method includes: receiving a compressed gene sequence that includes an identifier and difference data; extracting the difference data and the identifier from the compressed gene sequence for a current reference gene sequence; obtaining a current reference gene sequence from a reference data repository based on the identifier of the current reference gene sequence; and decompressing the compressed gene sequence based on the current reference gene sequence and the difference data, thereby producing a decompressed gene sequence.

In one embodiment of the present invention, there is provided an apparatus for determining similarity between a first gene sequence and a second gene sequence. The apparatus includes: a memory; a processor device communicatively coupled to the memory; and a module for determining similarity between a first gene sequence and a second gene sequence configured to carry out the steps of a computer-implemented method including: moving a sliding window of a predefined length on the first gene sequence and the second gene sequence respectively; extracting a first part $String1_i$ of the first gene sequence within the sliding window and a second part $String2_i$ of the second gene sequence within the sliding window during the $i^{th}$ movement of the sliding window; and determining the similarity between the first gene sequence and the second gene sequence based on the first part $String1_i$ and the second part $String2_i$.

In one embodiment of the present invention, there is provided an apparatus for compressing a gene sequence. The apparatus includes: a memory; a processor device communicatively coupled to the memory; and a module for compressing a gene sequence configured to carry out the steps of a computer-implemented method including: obtaining a gene sequence and at least one reference gene sequence; determining at least one similarity between the gene sequence and each of the at least one reference gene sequence; selecting the at least one reference gene sequence as a current reference gene sequence where the at least one similarity has a minimum value being less than or equal to a predefined threshold; and generating a compressed gene sequence including an identifier of the current reference gene sequence and difference data between the gene sequence and the current reference gene sequence.

In one embodiment of the present invention, there is provided an apparatus for decompressing a compressed gene sequence. The apparatus includes: a memory; a processor device communicatively coupled to the memory; and an extracting module for decompressing a compressed gene sequence configured to carry out the steps of a computer-implemented method including: receiving a compressed gene sequence that includes difference data and an identifier; extracting the difference data and the identifier from the compressed gene sequence for a current reference gene sequence; obtaining the current reference gene sequence from a reference data repository based on the identifier of the current reference gene sequence; and decompressing the compressed gene sequence based on the current reference gene sequence and the difference data.

By means of the technical solution according to the embodiments of the present invention, similarity between two gene sequences can be measured in a way that is more suitable for inherent characteristics of gene sequences; further, the most matched reference gene sequence can be found in the reference data repository based on the similarity; further, the to-be-stored gene sequence can be stored in compression.

BRIEF DESCRIPTION OF THE SEVERAL VIEWS OF THE DRAWINGS

Through the more detailed description of some embodiments of the present invention in the accompanying drawings, the above and other objects, features and advantages of the present invention will become more apparent, wherein the same reference generally refers to the same components in the embodiments of the present invention.

DETAILED DESCRIPTION OF THE PREFERRED EMBODIMENTS

Some preferable embodiments will be described in more detail with reference to the accompanying drawings, in which the preferable embodiments of the present invention have been illustrated. However, the present invention can be implemented in various manners, and thus should not be construed to be limited to the embodiments disclosed herein. On the contrary, those embodiments are provided for the thorough and complete understanding of the present invention, and completely conveying the scope of the present invention to those skilled in the art.

Figure 1:
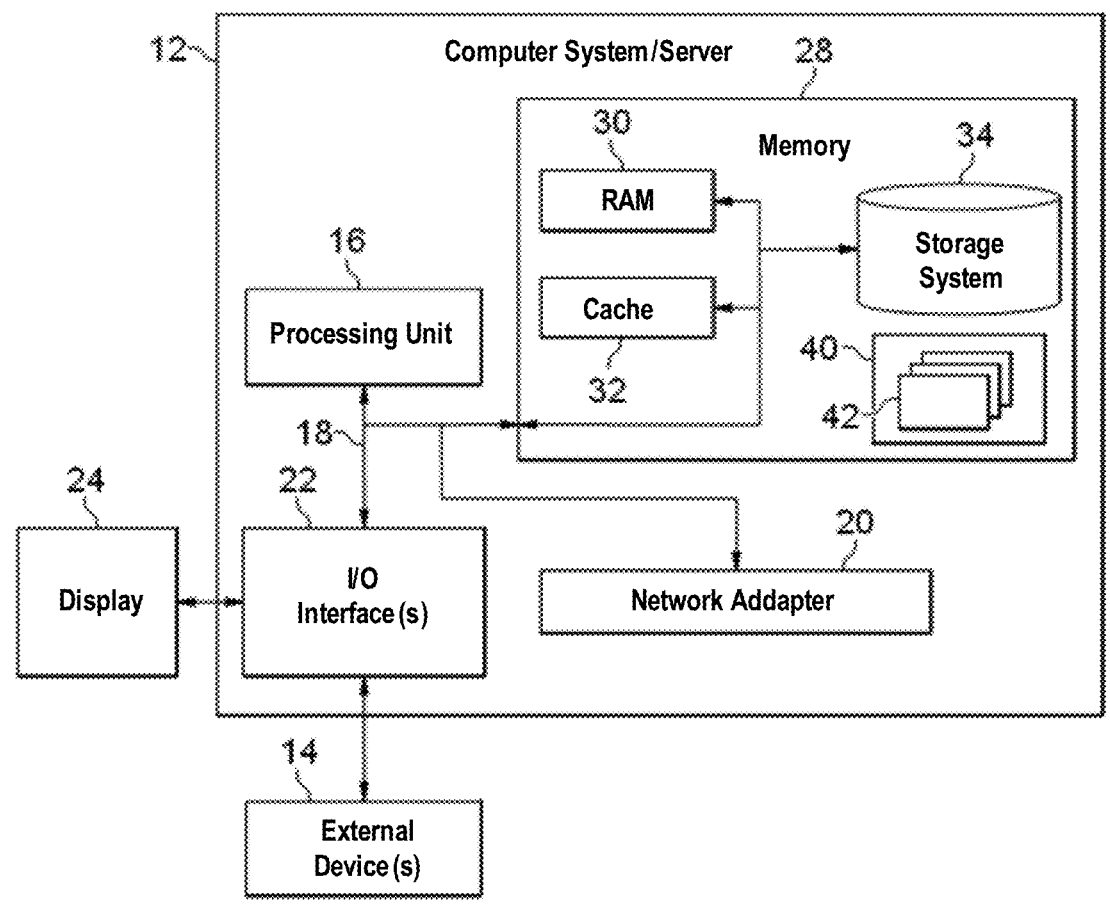
FIG. 1 schematically shows an exemplary computer system which is applicable to implement the embodiments of the present invention.

Referring now to FIG. 1, in which exemplary computer system/server 12 which is applicable to implement the embodiments of the present invention is shown. Computer system/server 12 is only illustrative and is not intended to suggest any limitation as to the scope of use or functionality of embodiments of the invention described herein.

As shown in FIG. 1, computer system/server 12 is shown in the form of a general-purpose computing device. The components of computer system/server 12 can include one or more processors or processing units 16, system memory 28, and bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media can be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 can further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 can include at least one program product having a set (e.g., at least one) of program modules that are configured to carry out the functions of embodiments of the invention.

Program/utility 40, having a set (at least one) of program modules 42, can be stored in memory 28 by way of example, and not limitation, as well as an operating system, one or more application programs, other program modules, and program data. Each of the operating system, one or more application programs, other program modules, and program data or some combination thereof, can include an implementation of a networking environment. Program modules 42 generally carry out the functions and/or methodologies of embodiments of the invention as described herein.

Computer system/server 12 can also communicate with one or more external devices 14 such as a keyboard, a pointing device, display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

Figure 2:
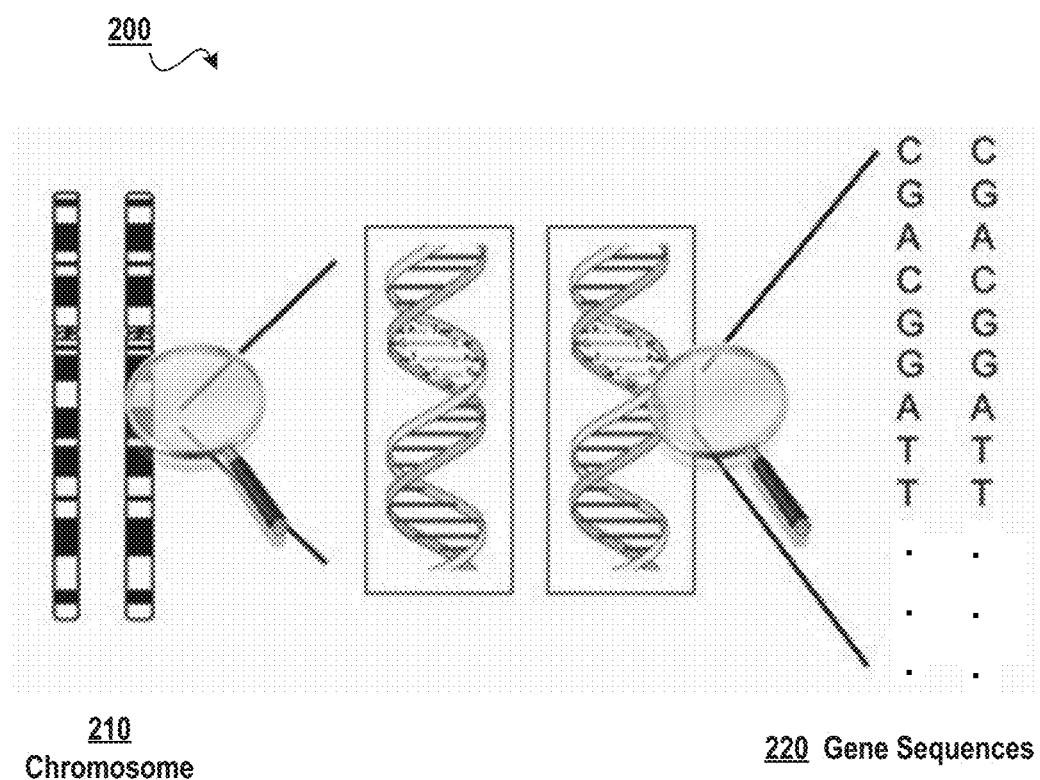
FIG. 2 schematically shows a diagram of data structure of gene sequences resulting from sequencing an organism.

FIG. 2 schematically shows diagram 200 of the data structure of a gene sequence obtained from sequencing an organism. In this figure, chromosome 210 and gene sequence 220 are shown as schematic diagrams. A gene sequence of an organism can be described by accurate arrangement of base pairs of deoxyribonucleic acid (DNA). The gene sequence can be represented by an ordered sequence constructed by four bases: A, G, T and C. Gene sequences of different organisms have different lengths. For example, human gene sequences have 3 billion base pairs or 6 billion characters, while gene sequences of other organisms can have different lengths.

Note that the gene sequence in the context of the present invention does not necessarily include all base pairs of one biological sample, but can include only one part of all base pairs such as only the part associated with human appearance.

Although a gene sequence can be represented by a text character string, the gene sequence still has other characteristics. In a conventional technical solution measuring similarity between text character strings is usually determined by comparing characters (or words) one by one. However, the gene sequence is a character sequence formed by A, G, T and C bases and have lengths of several billion orders of magnitude. So, when this conventional technical solution for measuring similarity between ordinary text character strings is applied to the gene sequence field, the effect of measurement is rather unsatisfactory.

Note that individual bases in the gene sequence cannot represent features of the biological sample, but a character string consisting of multiple characters can describe features of the biological sample. Therefore, the method for comparing characters in a text character string one by one in the prior art is not suitable for gene sequence processing.

Furthermore, gene sequences include consecutively arranged bases and while a gene sequence can be divided into multiple segments based on functions of various parts in the gene sequence, there is no concept of a "word" in the gene sequence as there is in a conventional text string. Therefore, the method for determining similarity based on words in the prior art is also ineffective in the gene sequence field.

Based on the above drawbacks in the prior art, the embodiments of the present invention propose a technical solution for determining similarity between two gene sequences based on a sliding window. Specifically, the present invention provides a method for determining similarity between a first gene sequence and a second gene sequence, including: moving a sliding window of a predefined length on the first gene sequence and the second gene sequence; during the $i^{th}$ movement of the sliding window, extracting a first part $String1_i$ of the first gene sequence within the sliding window, and a second part $String2_i$ of the second gene sequence within the sliding window; and determining the similarity between the first gene sequence and the second gene sequence based on the first part $String1_i$ and the second part $String2_i$.

Figure 3:
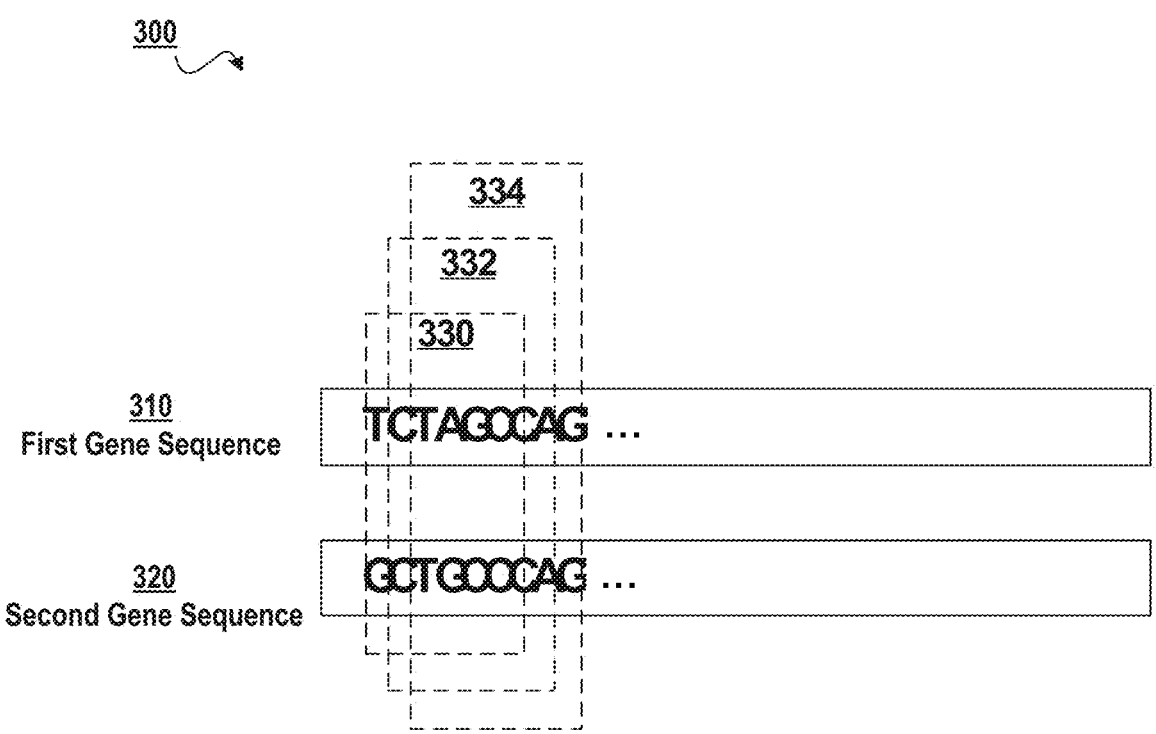
FIG. 3 schematically shows a block diagram of a technical solution for determining similarity between a first gene sequence and a second gene sequence according to one embodiment of the present invention.

FIG. 3 schematically shows block diagram 300 of a technical solution for determining similarity between a first gene sequence and a second gene sequence according to one embodiment of the present invention. In FIG. 3, first gene sequence 310 and second gene sequence 320 is shown. Both gene sequences are character strings including characters A, G, T and C. Sliding windows 330, 332, and 334 have a length of K corresponding to the number of individual bases captured by the sliding window. In FIG. 3, the value of K is set to seven (7). Sliding windows 330, 332, 334 can move on first gene sequence 310 and second gene sequence 320 so that the similarity between the two gene sequences can be determined by comparing a first part and a second part within the sliding window during each movement.

Sliding windows 330, 332, and 334 correspond to movements of a sliding window along the gene sequences where the first part of the sliding window is from first gene sequence 310 and the second part of the sliding window is from gene sequence 320. The first movement is sliding window 330, at which point the first part is a character string "TCTAGCC" and the second part is a character string "GCTGCCC." The second movement is sliding window 332, at which point the first part is a character string "CTAGCCA" and the second part is a character string "CTGCCCA." The third movement is sliding window 334, at which point the first part is a character string "TAGCCAG" and the second part is a character string "TGCCCAG."

In this embodiment, parts of the first gene sequence and the second gene sequence within the sliding window during each movement can be used as basic units for similarity comparison. Subsequently, the similarity between the two gene sequences can be determined based on a comparison of basic units during each movement of the sliding window.

Figure 4:
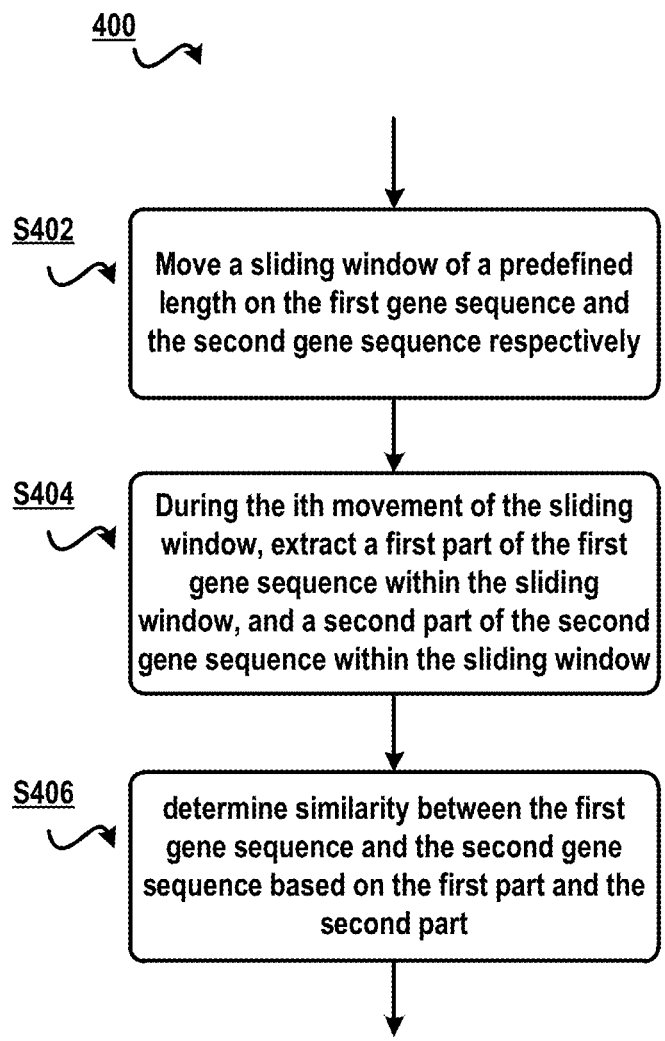
FIG. 4 schematically shows a flowchart of a method for determining similarity between a first gene sequence and a second gene sequence according to one embodiment of the present invention.

Referring to FIG. 4, flowchart 400 illustrates a method for determining similarity between a first gene sequence and a second gene sequence according to an embodiment of the present invention. In step S402, a sliding window of a predefined length is moved on the first gene sequence and the second gene sequence respectively.

In step S404, during the $i^{th}$ movement of the sliding window, a first part $String1_i$ of the first gene sequence within the sliding window, and a second part $String2_i$ of the second gene sequence within the sliding window are extracted. Note that since a character sequence having a short length (e.g. equal to 3) cannot represent biological features of a biological sample, it is inadvisable to set the length of the sliding window too short.

Those skilled in the art may understand that in the context of the present invention, i is a positive integer and its value is less than or equal to the number of movements of the sliding window on the two gene sequences. A maximum value of i depends on the length of the gene sequence, the length of the sliding window and movement stepsize. Those skilled in the art can calculate the maximum value based on principles of the sliding window, which are not detailed here.

Further, the larger the length of the sliding window, the lower the probability that the first part and the second part are matched. Where the length of the sliding window is too large (e.g. equal to 20), only when all of the 20 characters in the first part are completely same as 20 characters in the second part, will it be considered that the first part and the second part are the same. Therefore, if the length of the sliding window is too large, then a match between some character strings of short length within the first gene sequence and the second gene sequence may be neglected.

In one embodiment of the present invention, those skilled in the art can define the length of the sliding window. For example, those skilled in the art can select the length from a range between 4 and 12 based on demands of the concrete application environment, and specifically, can define the length of the sliding window as 7 or another value.

In step S406, the similarity between the first gene sequence and the second gene sequence is determined based on the first part $String1_i$ and the second part $String2_i$. In this step, those skilled in the art can determine the similarity between the two gene sequences on the basis of the process described with reference to FIG. 3.

In one embodiment of the present invention, moving the sliding window of a predefined length on the first gene sequence and the second gene sequence, respectively, includes: moving the sliding window at a stepsize that is less than or equal to the predefined length. Those skilled in the art should note since various parts within the first gene sequence and the second gene sequence have to be compared consecutively, the sliding stepsize can be set as less than or equal to the predefined length of the sliding window.

Specifically, the sliding stepsize can be set as 1. In this manner, every time the sliding window slides for a distance of 1 character, more comprehensive consideration can be given to each character string in the gene sequence and the sequential order between various character strings, so that the similarity between the two gene sequences can be determined more accurately. Alternatively, considering that bases represented by characters appear in pairs, the sliding stepsize can further be set as 2 for example.

In various embodiments of the present invention, the lengths of the first gene sequence and the second gene sequence can be the same or different. When the two gene sequences have the same length, with the movement of the sliding window, the first part and the second part formed during each movement can be compared one by one. When the lengths are different, missing characters can be completed by null characters. For example, suppose the first gene sequence has 2 more characters than the second gene sequence and the length of the sliding window is 7, then during the last movement of the sliding window, the first part of the first gene sequence can include 7 characters while the second part of the second gene sequence only includes 5 characters. At this point, it can be considered that the end of the second part further includes two null characters.

In one embodiment of the present invention, the determining the similarity between the first gene sequence and the second gene sequence based on the first part $String1_i$ and the second part $String2_i$ includes: during the $i^{th}$ movement of the sliding window, calculating local similarity $similarity_i$ between the first part $String1_i$ and the second part $String2_i$; and determining the similarity between the first gene sequence and the second gene sequence based on the first part $String1_i$ and the second part $String2_i$ based on the local similarity $similarity_i$.

In this embodiment, the local similarity $similarity_i$ refers to text similarity between the first part and the second part during one movement of the sliding window. Those skilled in the art can determine the local similarity $similarity_i$ based on various algorithms that are currently known or to be developed later.

In one embodiment of the present invention, the calculating local similarity $similarity_i$ between the first part $String1_i$ and the second part $String2_i$ includes: calculating the local similarity $similarity_i$ based on an edit distance $d_i$ between the first part $String1_i$ and the second part $String2_i$.

Edit distance is also referred to as Levenshtein distance, which refers to the minimum number of edits required to change one character string into the other. Allowed edits include: substituting one character with another, inserting one character, and deleting one character.

For example, the following 3 edits are required to change kitten into sitting:

sitten (k→s)
sittin (e→i)
sitting (→g)

Those skilled in the art should understand since the gene sequence only involves combinations of 4 characters A, G, T and C, in the context of the present invention different weights can further be set to different characters, or different weights can be set to different operation types, etc. Further, those skilled in the art can modify the specific formula for calculating edit distance based on biological meaning of various combinations of characters.

Figure 5:
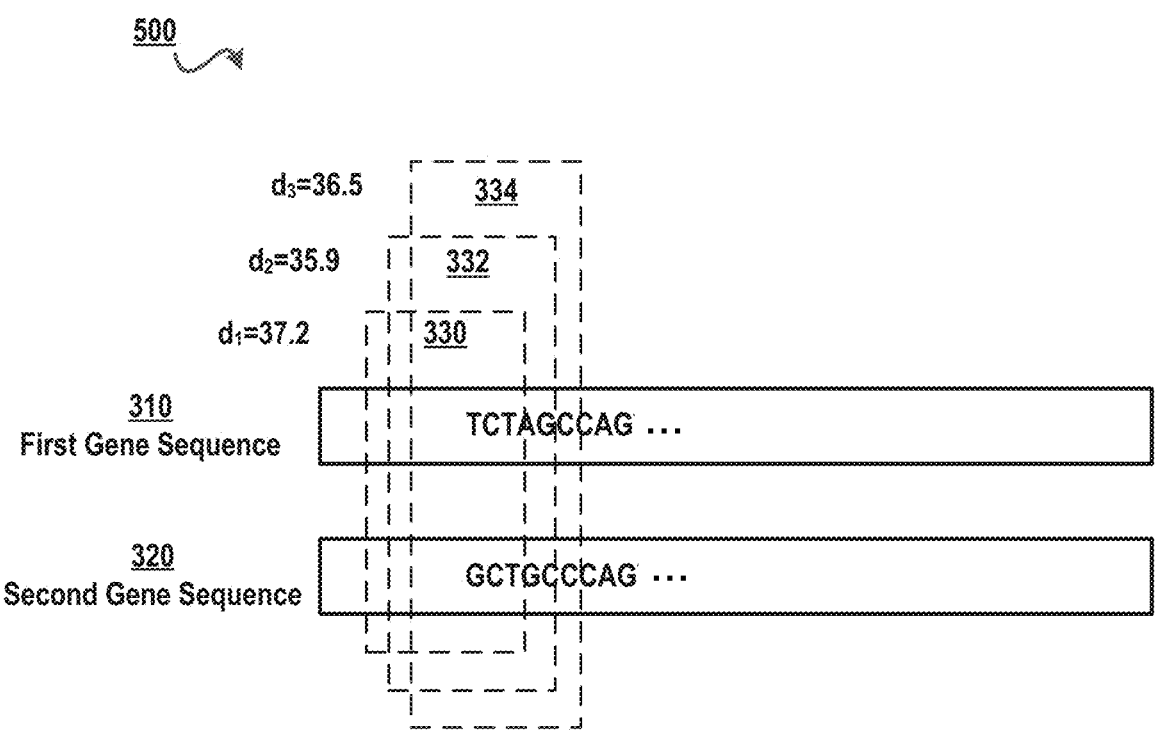
FIG. 5 schematically shows a schematic view of the process for determining similarity between a first gene sequence and a second gene sequence according to one embodiment of the present invention.

FIG. 5 schematically shows diagram 500 of the process for determining similarity between a first gene sequence and a second gene sequence according to one embodiment of the present invention. As shown in FIG. 5, edit distance between two character strings within sliding window 330 $d_1$=37.2, edit distance between two character strings within sliding window 332 $d_2$=35.9, and edit distance between two character strings within sliding window 334 $d_3$=36.5. Those skilled in the art can further calculate an edit distance between two character strings during each movement of the sliding window based on the formula for calculating the edit distance. Note the three edit distances shown in this embodiment are only illustrative, and those skilled in the art can design the specific calculation formula.

In one embodiment of the present invention, the edit distance $d_i$ can directly be used as the local similarity similarity$_i$ between the first part String1$_i$ and the second part String2$_i$. In another embodiment of the present invention, local similarity similarity$_i$ can further be calculated as a function of the edit distance $d_i$, for example, define similarity$_i$=$d_i^2$ or those skilled in the art can further calculate local similarity similarity$_i$ based on another formula. Subsequently, the similarity between the two gene sequences can be calculated on the basis of the local similarity similarity$_i$ resulting from each movement of the sliding window.

In one embodiment of the present invention, determining the similarity between the first gene sequence and the second gene sequence based on the local similarity similarity$_i$ includes: calculating the similarity based on a formula similarity=$\Sigma_{i=1}^{N}$similarity$_i$, wherein N is the number of movements of the sliding window.

In this embodiment, the local similarity similarity$_i$ resulting from each movement of the sliding window can be added up to obtain the similarity between the first gene sequence and the second gene sequence. Or those skilled in the art can further use another formula for calculating the similarity.

In one embodiment of the present invention, the first gene sequence is a part from a first sequence, and the second gene sequence is a part from a second sequence. Note that a huge computation amount will be involved when the length of the gene sequence is very large. For example, when determining similarity between a first gene sequence of 6 billion characters describing human gene information and a second gene sequence of 6 billion characters describing human gene information. Therefore, the gene sequence can be divided into a plurality of segments such as 10 thousand character strings, and at each time processing is performed only to data within a segment of small length.

In one embodiment of the present invention, it is not intended to limit whether there is an overlapping area between resulting segments. For example, segments can be divided to include an overlapping area so that various resulting segments can be spliced as a raw gene sequence.

Although the specific example of how to calculate similarity between two gene sequences has been illustrated above, those skilled in the art should understand before selecting an appropriate reference gene sequence from the reference data repository, similarity between the to-be-stored gene sequence and various reference gene sequences in the reference data repository has to be calculated further.

In one embodiment of the present invention, when there are a plurality of reference gene sequences, it will take more time to determine similarity between the to-be-stored gene sequence and the plurality of reference gene sequences (for example, n). Therefore, the to-be-stored gene sequence can be aligned with n reference gene sequences according to the manner as shown in FIG. 5, and the sliding window is moved from the header of each gene sequence. Thereby, during each movement of the sliding window, parts of the to-be-processed gene sequence and the n reference gene sequences within the sliding window can be obtained simultaneously. Next, the part of the to-be-stored gene sequence within the sliding window can be compared with corresponding parts of the n reference gene sequences within the sliding window respectively, so as to obtain corresponding local similarity.

To accelerate the computation speed, an edit distance that might be used in similarity calculation can be pre-calculated, and the pre-calculated edit distance is stored in a data table. Or new edit distances can be calculated with the movement of the sliding window, and an edit distance between two character strings that have once appeared is stored in the data table, so that the edit distance can be reused directly in subsequent processing.

Alternatively, in order to accelerate the computation speed, a lookup table for assisting in calculation can be set, which can include: character strings within the sliding window when the sliding window moves along various reference gene sequences; and information recording in which reference gene sequences the above character strings once have appeared. Specifically, with reference to FIG. 5, suppose first gene sequence 310 is the to-be-stored gene sequence, while second gene sequence 320 is the reference gene sequence; when the sliding window is at the location shown by a reference numeral 330, a character string of the reference gene sequence within the sliding window is "GCTGCCC." If the character string further appears in a $3^{rd}$ reference gene sequence, . . . , $i^{th}$ reference gene sequence, . . . , and $n^{th}$ reference gene sequence, then a lookup table can be as shown in Table 1 below.

TABLE 1

Lookup Table

| No. | Character string | Reference gene sequence |
|---|---|---|
| 1 | GCTGCCC | 1, 3, . . . , i, . . . , n |
| . . . . . . | | . . . |

Note Table 1 merely illustrates a plurality of reference gene sequences including the character string "GCTGCCC," and those skilled in the art can further obtain corresponding reference gene sequences including other character strings. By means of the lookup table as shown in Table 1, all reference gene sequences including the character string "GCTGCCC" can further be found in the lookup table; thereby, similarity between the to-be-stored gene sequence and each of these found reference gene sequence can be increased by an edit distance between the character strings "TCTAGCC" and "GCTGCCC" (in the embodiment shown in FIG. 5, the edit distance equals 37.2). By adding up edit distances based on the lookup table, similarity between the to-be-stored gene sequence and various reference gene sequences can be obtained.

Note the method for determining similarity of the present invention can serve as a basic operation of gene sequence processing, and this method can further act as a substep for various processing such as selecting an appropriate reference gene sequence from the reference data repository, clustering a plurality of gene sequences based on similarity between the plurality of gene sequences, and determining a clustering center.

With reference to the accompanying drawings, detailed description is presented below to information of a method for selecting a reference gene sequence and further compressing and decompressing a to-be-stored gene sequence. So far there are many organizations that can provide reference gene sequences and these reference gene sequences can be accessed through networking. According to the embodiments of the present invention, when compressing a gene sequence, only difference data between the gene sequence and a reference gene sequence and an identifier of the reference gene sequence have to be stored, and then raw data of the gene sequence can be obtained on the basis of the stored difference data and the reference gene sequence obtained through network access.

In one embodiment of the present invention, there is proposed a method for compressing a gene sequence, including: obtaining a gene sequence and at least one reference gene sequence; determining at least one similarity between the gene sequence and each of the at least one reference gene sequence by means of a method according to the present invention; in response to a minimum value in the at least one similarity being less than or equal to a predefined threshold, selecting the reference gene sequence whose similarity is the minimum value as a current reference gene sequence; and generating a compressed gene sequence, the compressed gene sequence including an identifier of the current reference gene sequence and difference data between the gene sequence and the current reference gene sequence.

Figure 6:
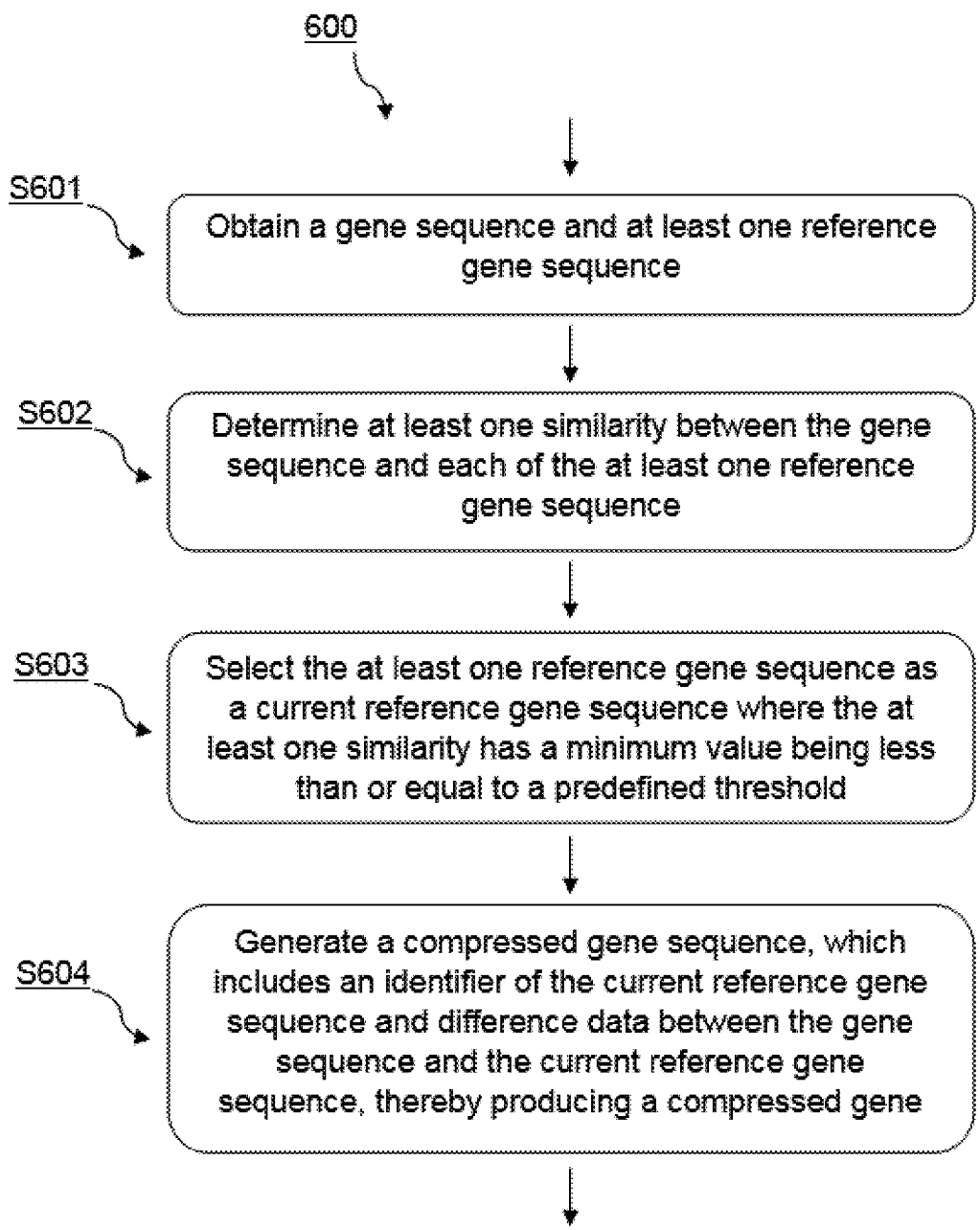
FIG. 6 schematically shows a flowchart of a method for compressing a gene sequence according to one embodiment of the present invention.

FIG. 6 schematically shows flowchart 600 of a method for compressing a gene sequence according to one embodiment of the present invention. In step S601, a gene sequence and at least one reference gene sequence is obtained. In step S602, in response to obtaining the gene sequence and at least one reference gene sequence, at least one similarity between the gene sequence and each of the at least one reference gene sequence is determined by means of the above method. Those skilled in the art can calculate similarity between each reference gene sequence and the to-be-compressed gene sequence one by one based on the method described with reference to FIGS. 3 to 5 above.

In step S603, in response to a minimum value in the at least one similarity being less than or equal to a predefined threshold, the reference gene sequence whose similarity is the minimum value is selected as a current reference gene sequence. In this embodiment, when similarity between two gene sequences is measured by "distance," the reference gene sequence with a minimum value of the similarity can be selected as a current reference gene sequence. Alternatively, when "similarity degree" is used as a measurement criterion, the reference gene sequence with a maximum value of the similarity can be used as a current reference gene sequence. Those skilled in the art can define specific implementation based on the principle of the present invention.

In step S604, a compressed gene sequence is generated, the compressed gene sequence including an identifier of the current reference gene sequence and difference data between the gene sequence and the current reference gene sequence. Since the selected current reference gene sequence is a reference gene sequence in the reference data repository which has the highest similarity degree with the to-be-compressed reference gene sequence, all information of the to-be-compressed gene sequence can be saved simply by storing an identifier of the current reference gene sequence and difference data between the to-be-compressed gene sequence and the current reference gene sequence.

Since the compressed gene sequence does not include portions of the to-be-compressed gene sequence that are common to the current reference gene sequence, the space occupied by the to-be-compressed gene sequence can be reduced greatly. When the reference data repository only includes one reference gene sequence, the identifier of the reference gene sequence does not need to be included in the to-be-compressed gene sequence; when the reference data repository includes a plurality of reference gene sequences, identifiers of the reference gene sequences need to be included in the to-be-compressed gene sequence, so that which reference gene sequence is used in compressed can be found through the identifier.

In one embodiment of the present invention, the generating a compressed gene sequence includes: in response to there being an annotation in the gene sequence, including an identifier and a position of the annotation in the compressed gene sequence; and including in the compressed gene sequence difference data between a part of the gene sequence and a corresponding part of the current reference gene sequence, the part of the gene sequence being a part that is irrelevant to the annotation.

With the human research on gene sequences, meaning of some gene sequence segments can be determined so far. Therefore, current storage of gene sequences can support annotation with reference to a gene sequence segment. The annotation information here can be, for example, annotation information describing functions of a gene sequence between given starting and ending positions. For example, suppose a gene sequence between starting and ending positions that are 1 and 10000 respectively is a gene sequence related to black hair, then an annotation can be added with respect to the segment between positions 1 and 10000, which indicates that this gene sequence part is related to black hair. Since content of a gene sequence segment related to a given function is usually fixed (or only has minor difference), only an identifier of the annotation can be recorded in the compressed gene sequence, rather than recording the gene sequence segment per se associated with the annotation.

In addition, since human beings belong to mammals, human gene sequences include some conserved gene sequence segments that are common to lower mammals. Although human beings can further be subdivided into different races, gene sequences of each race include these fixed gene sequence segments. Therefore, these fixed gene sequence segments can be replaced by identifiers of annotations. In this manner, the storage space can be saved significantly.

Figure 7A:
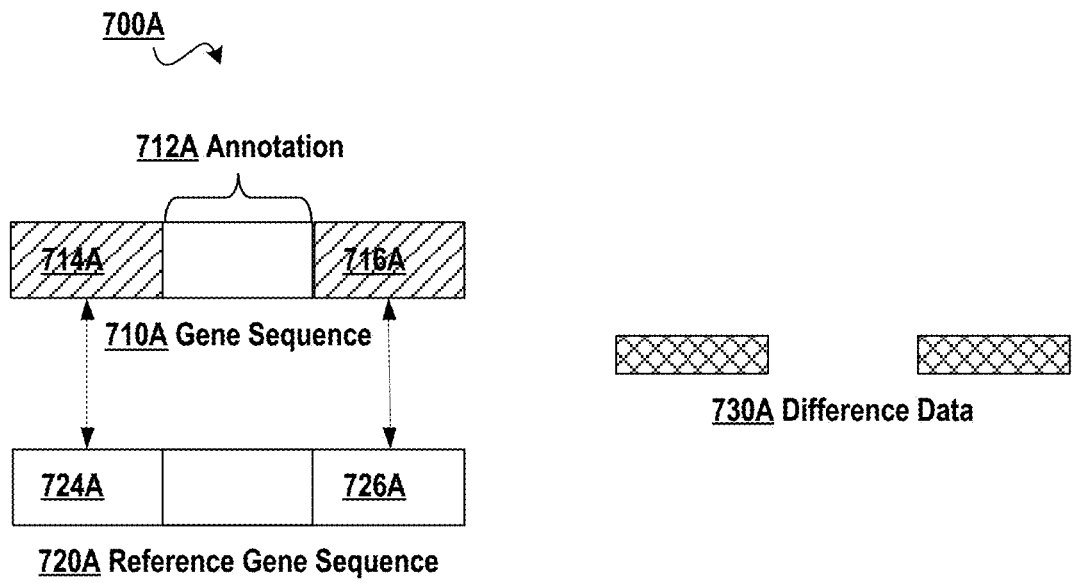
FIGS. 7A and 7B schematically show block diagrams of respectively processing an annotation and a segment during compression according to one embodiment of the present invention.

FIG. 7A schematically shows block diagram 700A of processing an annotation during compression according to one embodiment of the present invention. In FIG. 7A, suppose one segment of a to-be-compressed gene sequence includes annotation 712A, while other segments 714A and 716A do not include the annotation. When generating a compressed gene sequence, difference data different from the reference gene sequence does not need to be obtained for the part including annotation 712A. Instead, only an identifier of annotation 712A is recorded. Regarding other parts that do not include the annotation (i.e., segments 714A and 716A), difference data 730 between the two segments and corresponding segments (724A and 726A) in the reference gene sequence is obtained according to the method described above.

Although FIG. 7A illustrates a circumstance where one annotation is included, when to-be-compressed gene sequence 710A includes a plurality of annotations, those skilled in the art can further process each annotation based on the above principle.

In one embodiment of the present invention, the generating a compressed gene sequence includes: dividing the gene sequence into a plurality of segments; with respect to each segment among the plurality of segments, searching for a matched part to each segment in the current reference gene sequence; including in the compressed gene sequence a position of the matched part in the current reference gene sequence and difference data between the each segment and the matched part.

When a to-be-compressed gene sequence is so long as to find an appropriate reference gene sequence, the to-be-compressed gene sequence can further be divided into a plurality of segments, and processing is performed with respect to each segment. For example, the to-be-compressed gene sequence can be divided into fixed-length segments or divided into segments based on biological meaning of the gene sequence.

Figure 7B:
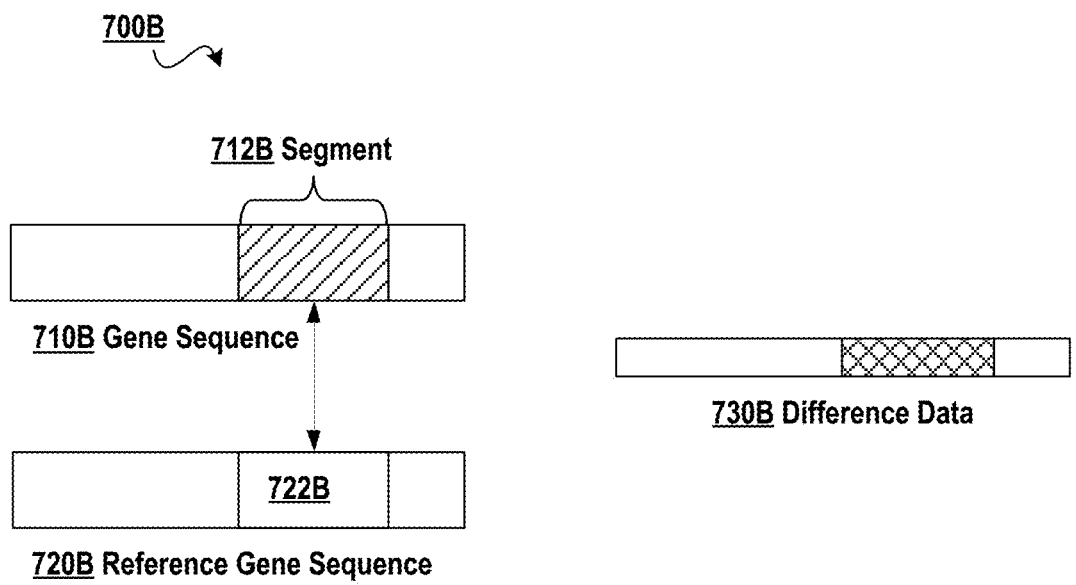

FIG. 7B schematically shows block diagram 700B of processing segments during compression according to one embodiment of the present invention. In FIG. 7B, suppose gene sequence 710B includes segment 712B, then a matched part to segment 712B can be looked for in reference gene sequence 720B. For example, segment 722B is found in reference gene sequence 720B. Therefore, a position of segment 722B in reference gene sequence 720B can be recorded, and difference data between segment 712B in gene sequence 710B and segment 722B in reference gene sequence 720B can be obtained.

Although FIG. 7B illustrates a circumstance where one segment is included, when to-be-compressed gene sequence 710B includes a plurality of segments, those skilled in the art can further process each segment based on the above principle.

In one embodiment of the present invention, there is further included: in response to the minimum value in the at least one similarity being larger than the predefined threshold, assigning the gene sequence and other to-be-compressed gene sequences to at least one cluster, wherein similarity between each of the other to-be-compressed gene sequences and any of the at least one reference gene sequence is larger than the predefined threshold; and generating a compressed gene sequence, the compressed gene sequence including an indicator of a clustering center of a cluster to which the gene sequence belongs, as well as difference data between the gene sequence and the clustering center.

In this embodiment, if the minimum value in the resulting at least one similarity is larger than the predefined threshold, this means there is no reference gene sequence matched to the to-be-compressed gene sequence. In this case, the to-be-compressed gene sequence and other gene sequences for which no matched reference gene sequences are found can be clustered, and the obtained clustering center can be used as a new reference criterion for compression.

In one embodiment of the present invention, new reference gene sequences can be gradually added to the reference data repository. For example, the reference data repository can be gradually updated when compressing the gene sequence. Specifically, regarding a newly inputted gene sequence A, when a reference gene sequence with high similarity cannot be found in the reference data repository, it can be considered that gene sequence A can belong to a new species and thus can be added to a candidate list. When gene sequences in the candidate list amount to a certain number, a clustering method can be applied and the most representative to-be-compressed gene sequence obtained from clustering is added to the reference data repository.

In one embodiment of the present invention, there is further provided a method for decompressing a compressed gene sequence resulting from the above method. Specifically, there is provided a method for decompressing a compressed gene sequence, including: in response to receiving a compressed gene sequence resulting from the compression method of the present invention, extracting difference data and an identifier of a current reference gene sequence from the compressed gene sequence; obtaining the current reference gene sequence from a reference data repository based on the identifier of the current reference gene sequence; and decompressing the compressed gene sequence based on the current reference gene sequence and the difference data.

Figure 8:
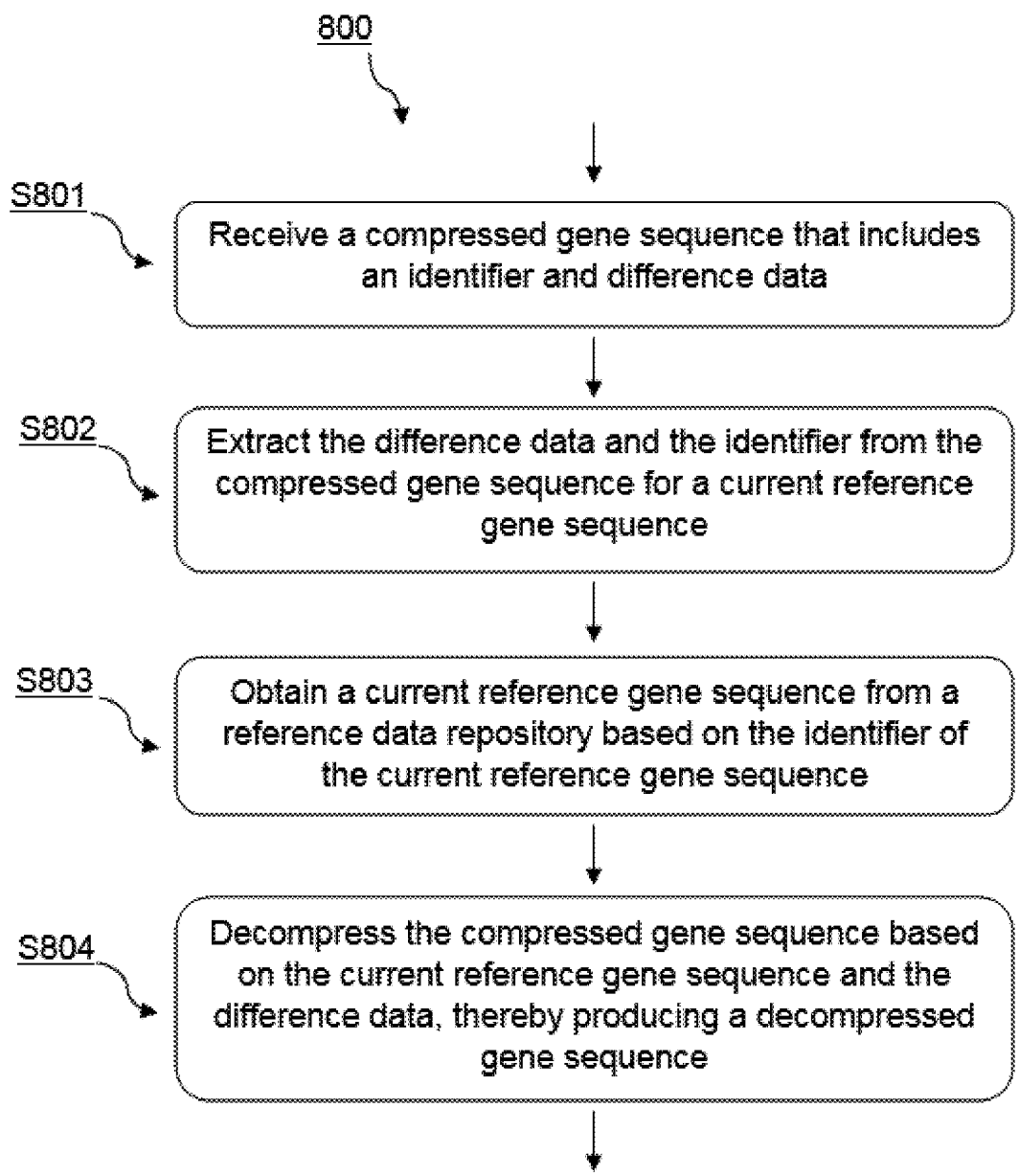
FIG. 8 schematically shows a flowchart of a method for decompressing a compressed gene sequence according to one embodiment of the present invention.

FIG. 8 schematically shows flowchart 800 of a method for decompressing a compressed gene sequence according to one embodiment of the present invention. In step S801, a compressed gene sequence is received. In step S802, in response to receiving a compressed gene sequence resulting from the compression method of the present invention, difference data and an identifier of a current reference gene sequence are extracted from the compressed gene sequence.

In step S803, a current reference gene sequence is obtained from a reference data repository based on the identifier of the current reference gene sequence. A current reference gene sequence can be obtained from a reference data repository. Since the compressed gene sequence saves an identifier of the current gene sequence that is used in compressing the gene sequence, the reference gene sequence can be obtained from the reference data repository through the identifier.

In step S804, the compressed gene sequence is decompressed based on the reference gene sequence and the difference data. Since the difference data in the compressed gene sequence saves difference data between the gene sequence and the current reference gene sequence, the difference data can be applied to the reference gene sequence so as to restore a raw gene sequence from the compressed gene sequence.

Various embodiments implementing the method of the present invention have been described above with reference to the accompanying drawings. Those skilled in the art can understand that the method can be implemented in software, hardware or a combination of software and hardware. Moreover, those skilled in the art can understand by implementing steps in the above method in software, hardware or a combination of software and hardware, there can be provided an apparatus based on the same invention concept. Even if the apparatus has the same hardware structure as a general-purpose processing device, the functionality of software contained therein makes the apparatus manifest distinguishing properties from the general-purpose processing device, thereby forming an apparatus of the various embodiments of the present invention. The apparatus described in the present invention includes several means or modules, the means or modules configured to execute corresponding steps.

Upon reading this specification, those skilled in the art can understand how to write a program for implementing actions performed by these means or modules. Since the apparatus is based on the same invention concept as the method, the same or corresponding implementation details are also applicable to means or modules corresponding to the method. As detailed and complete description has been presented above, the apparatus is not detailed below.

Figure 9A:
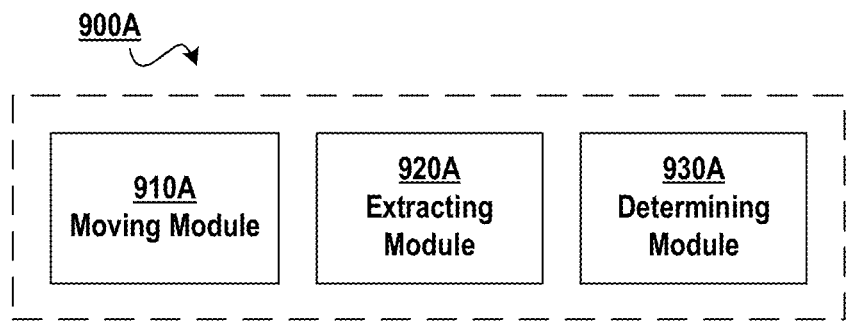
FIG. 9A schematically shows a block diagram of an apparatus for determining similarity between a first gene sequence and a second gene sequence according to one embodiment of the present invention.

FIG. 9A schematically shows block diagram 900A of an apparatus for determining similarity between a first gene sequence and a second gene sequence. Specifically, there is provided an apparatus for determining similarity between a first gene sequence and a second gene sequence, including: moving module 910A configured to move a sliding window of a predefined length on the first gene sequence and the second gene sequence respectively; extracting module 920A configured to, during the $i^{th}$ movement of the sliding window, extract a first part $String1_i$ of the first gene sequence within the sliding window, and a second part $String2_i$ of the second gene sequence within the sliding window; and determining module 930A configured to determine similarity between the first gene sequence and the second gene sequence based on the first part $String1_i$ and the second part $String2_i$.

In one embodiment of the present invention, moving module 910A includes: a window moving module configured to move the sliding window at a stepsize that is less than or equal to the predefined length.

In one embodiment of the present invention, determining module 930A includes: a calculating module configured to, during the $i^{th}$ movement of the sliding window, calculate local similarity $similarity_i$ between the first part $String1_i$ and the second part $String2_i$; and a similarity determining module configured to determine similarity between the first gene sequence and the second gene sequence based on the local similarity $similarity_i$.

In one embodiment of the present invention, the calculating module includes: a local similarity calculating module configured to calculate the local similarity $similarity_i$ based on an edit distance $d_i$ between the first part $String1_i$ and the second part $String2_i$.

In one embodiment of the present invention, the similarity determining module includes: a solving module configured to calculate the similarity based on a formula $similarity=\Sigma_{i=1}^{N}similarity_i$, wherein N is the number of movements of the sliding window.

Figure 9B:
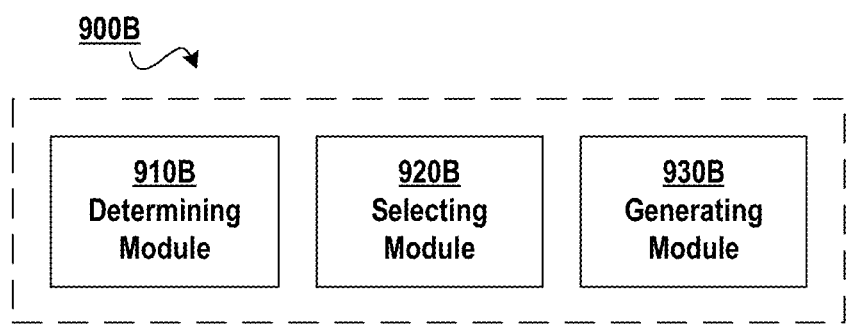
FIG. 9B schematically shows a block diagram of an apparatus for compressing a gene sequence according to one embodiment of the present invention.

FIG. 9B schematically shows an apparatus for compressing a gene sequence according to one embodiment of the present invention. Specifically, there is provided an apparatus for compressing a gene sequence, including: a determining module 910B configured to, in response to obtaining the gene sequence and at least one reference gene sequence, determine at least one similarity between the gene sequence and each of the at least one reference gene sequence by means of a method according to the present invention; selecting module 920B configured to, in response to a minimum value in the at least one similarity being less than or equal to a predefined threshold, select the reference gene sequence whose similarity is the minimum value as a current reference gene sequence; and generating module 930B configured to generate a compressed gene sequence, the compressed gene sequence including an identifier of the current reference gene sequence and difference data between the gene sequence and the current reference gene sequence.

In one embodiment of the present invention, generating module 930B includes: an annotation processing module configured to, in response to there being an annotation in the gene sequence, include an identifier and a position of the annotation in the compressed gene sequence; and a first inserting module configured to include in the compressed gene sequence difference data between a part of the gene sequence and a corresponding part of the current reference gene sequence, the part of the gene sequence being a part that is irrelevant to the annotation.

In one embodiment of the present invention, generating module 930B includes: a dividing module configured to divide the gene sequence into a plurality of segments; a search module configured to, with respect to each segment among the plurality of segments, search for a matched part to each segment in the current reference gene sequence; a second inserting module configured to include in the compressed gene sequence a position of the matched part in the current reference gene sequence and difference data between the each segment and the matched part.

In one embodiment of the present invention, there are further included: a clustering module configured to, in response to the minimum value in the at least one similarity being larger than the predefined threshold, assign the gene sequence and other to-be-compressed gene sequences to at least one cluster, wherein similarity between each of the other to-be-compressed gene sequences and any of the at least one reference gene sequence is larger than the predefined threshold; and a second generating module configured to generate a compressed gene sequence, the compressed gene sequence including an indicator of a clustering center of a cluster to which the gene sequence belongs, as well as difference data between the gene sequence and the clustering center.

Figure 9C:
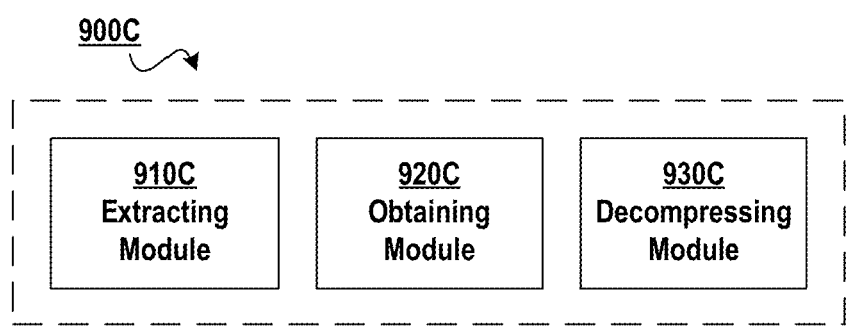
FIG. 9C schematically shows a block diagram of an apparatus for decompressing a compressed gene sequence according to one embodiment of the present invention.

FIG. 9C schematically shows block diagram 900C of an apparatus for decompressing a compressed gene sequence according to one embodiment of the present invention. Specifically, there is provided an apparatus for decompressing a compressed gene sequence, including: an extracting module 910C configured to, in response to receiving a compressed gene sequence resulting from the compression method of the present invention, extract difference data and an identifier of a current reference gene sequence from the compressed gene sequence; an obtaining module 920C configured to obtain a current reference gene sequence from a reference data repository based on the identifier of the current reference gene sequence; and decompressing module 930C configured to decompress the compressed gene sequence based on the reference gene sequence and the difference data.

By means of the technical solution according to the embodiments of the present invention, similarity between two gene sequences can be measured in a way that is more suitable for inherent characteristics of gene sequences; further, the most matched reference gene sequence can be found in the reference data repository based on the similarity, and further the to-be-stored gene sequence can be stored in compression.

The present invention can be a system, a method, and/or a computer program product. The computer program product can include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can include copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention can be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein includes an article of manufacture including instructions which implement aspects of the function/act specified in the flowchart and/or block diagram block or blocks.

The computer readable program instructions can also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods and computer program products according to various embodiments of the present invention. In this regard, each block in the flowchart or block diagrams can represent a module, segment, or portion of code, which includes one or more executable instructions for implementing the specified logical function(s). It should also be noted that, in some alternative implementations, the functions noted in the block can occur out of the order noted in the figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method for determining similarity between a first gene sequence of a first sample and a second gene sequence of a second sample, wherein the first sample is taken from a first organism and the second sample is taken from a second organism, the method comprising:
    moving a sliding window having a predefined length on the first gene sequence;
    moving the sliding window on the second gene sequence, simultaneously with moving the sliding window on the first gene sequence;

extracting a first part String1$_i$ of the first gene sequence that is present within the sliding window during an i$^{th}$ movement of the sliding window;

extracting a second part String2$_i$ of the second gene sequence that is present within the sliding window during the i$^{th}$ movement of the sliding window;

determining the similarity between the first gene sequence and the second gene sequence based on a similarity between the first part String1$_i$ and the second part String2$_i$, thereby identifying the similarity of the first gene sequence and second gene sequence;

selecting the first gene sequence as a reference gene sequence for the second gene sequence, based on the similarity between the first gene sequence and the second gene sequence meeting a predefined threshold;

storing the reference gene sequence in a memory device; and storing the second gene sequence in the memory device as an identifier for the reference gene sequence plus a difference between the reference gene sequence and the second gene sequence, thereby minimizing an amount of data from the second gene sequence that is stored in the memory device.

2. The computer-implemented method according to claim 1, wherein moving the sliding window on the first gene sequence and moving the sliding window on the second gene sequence further comprises:

moving the sliding window at a stepsize that is less than or equal to the predefined length.

3. The computer-implemented method according to claim 1, wherein determining the similarity between the first gene sequence and the second gene sequence based on the similarity between the first part String1$_i$ and the second part String2$_i$ during the i$^{th}$ movement of the sliding window, comprises:

calculating local similarity, similarity$_i$, between the first part String1$_i$ and the second part String2$_i$; and determining the similarity between the first gene sequence and the second gene sequence based on the local similarity, similarity$_i$.

4. The computer-implemented method according to claim 3, wherein calculating local similarity, similarity$_i$, between the first part String1$_i$ and the second part String2$_i$ comprises:

calculating the local similarity, similarity$_i$, based on an edit distance, d$_i$, between the first part String1$_i$ and the second part String2$_i$.

5. The computer-implemented method according to claim 3, wherein determining similarity between the first gene sequence and the second gene sequence based on the local similarity, similarity$_i$, comprises:

calculating the similarity between the first gene sequence and the second gene sequence based on a formula similarity=$\Sigma_{i=1}^{N}$similarity$_i$, wherein N is the number of movements of the sliding window.

6. An apparatus for determining similarity between a first gene sequence of a first sample and a second gene sequence of a second sample, wherein the first sample is taken from a first organism and the second sample is taken from a second organism, comprising:

a processor device; and a memory communicatively coupled to the processor device, the memory storing a program product that, when executed by the processor device, causes the processor device to carry out steps for determining a similarity between a first gene sequence and a second gene sequence, the steps comprising:

moving a sliding window of a predefined length on the first gene sequence;

moving the sliding window on the second gene sequence, simultaneously with moving the sliding window on the first gene sequence;

extracting a first part String1$_i$ of the first gene sequence that is present within the sliding window during an i$^{th}$ movement of the sliding window;

extracting a second part String2$_i$ of the second gene sequence that is present within the sliding window during the i$^{th}$ movement of the sliding window;

determining the similarity between the first gene sequence and the second gene sequence based on a similarity between the first part String1$_i$ and the second part String2$_i$;

selecting the first gene sequence as a reference gene sequence for the second gene sequence, based on the similarity between the first gene sequence and the second gene sequence meeting a predefined threshold;

storing the reference gene sequence in the memory; and storing the second gene sequence in the memory as an identifier for the reference gene sequence plus a difference between the reference gene sequence and the second gene sequence, thereby minimizing an amount of data from the second gene sequence that is stored in the memory.

7. The apparatus according to claim 6, wherein the moving the sliding window on the first gene sequence and the moving the sliding window on the second gene sequence further comprises:

moving the sliding window at a stepsize that is less than or equal to the predefined length.

8. The apparatus according to claim 6, wherein the determining step of the computer-implemented method further comprises:

calculating local similarity, similarity$_i$, between the first part String1$_i$ and the second part String2$_i$ during the i$^{th}$ movement of the sliding window; and determining the similarity between the first gene sequence and the second gene sequence based on the local similarity, similarity$_i$.

9. The apparatus according to claim 8, wherein the calculating step of the computer-implemented method further comprises:

calculating the local similarity, similarity$_i$, based on an edit distance, d$_i$, between the first part String1$_i$ and the second part String2$_i$.

10. The apparatus according to claim 8, wherein the calculating step of the computer-implemented method further comprises:

calculating the similarity between the first gene sequence and the second gene sequence based on a formula similarity=$\Sigma_{i=1}^{N}$similarity$_i$, wherein N is the number of movements of the sliding window.

11. The apparatus according to claim 7, wherein the i$^{th}$ movement of the sliding window is one of a plurality of movements of the sliding window, and wherein each movement of the plurality of movements is made at the same stepsize.

12. The apparatus according to claim 11, wherein the stepsize comprises a number of characters of the first gene sequence and of the second gene sequence by which the sliding window is shifted.

13. The apparatus according to claim 6, wherein the computer-implemented method further comprises:

extracting a third part of the first gene sequence that is present within the sliding window during an i+1$^{th}$ movement of the sliding window, wherein the third part of the first gene sequence contains a different character string from the first part of the first gene sequence;

extracting a fourth part of the second gene sequence that is present within the sliding window during the i+1$^{th}$ movement of the sliding window, wherein the fourth part of the second gene sequence contains a different character string from the second part of the second gene sequence, wherein the determining the similarity between the first gene sequence and the second gene sequence is further based on a similarity between the third part of the first gene sequence and the fourth part of the second gene sequence.

* * * * *